(12) United States Patent
Esrock

(10) Patent No.: US 9,687,328 B2
(45) Date of Patent: Jun. 27, 2017

(54) FULL FLOW DISPOSABLE SYRINGE TIP AND CONNECTOR

(71) Applicant: Bernard S. Esrock, Coronado, CA (US)

(72) Inventor: Bernard S. Esrock, Coronado, CA (US)

(*) Notice: Subject to any disclaimer, the term of this patent is extended or adjusted under 35 U.S.C. 154(b) by 506 days.

(21) Appl. No.: 14/268,080

(22) Filed: May 2, 2014

(65) Prior Publication Data

US 2014/0329198 A1 Nov. 6, 2014

Related U.S. Application Data

(60) Provisional application No. 61/819,114, filed on May 3, 2013, provisional application No. 61/939,444, filed on Feb. 13, 2014.

(51) Int. Cl.
*A61C 5/04* (2006.01)
*A61C 17/02* (2006.01)

(52) U.S. Cl.
CPC ..... *A61C 17/0202* (2013.01); *Y10T 29/49567* (2015.01)

(58) Field of Classification Search
CPC . A61C 17/02; A61C 17/0202; A61C 17/0214; A61C 17/028
USPC .................................. 433/80, 81, 84, 88–90
See application file for complete search history.

(56) References Cited

U.S. PATENT DOCUMENTS

| | | | |
|---|---|---|---|
| 1,683,350 A | 9/1928 | Hein | |
| 1,802,499 A | 4/1931 | Chapman | |
| 2,371,971 A | 3/1945 | Main et al. | |
| 2,452,275 A | 10/1948 | Woodling | |
| 2,561,827 A | 7/1951 | Soos | |
| 2,833,567 A | 5/1958 | Bacher et al. | |
| 2,873,985 A | 2/1959 | Baldwin, Jr. | |
| 2,978,262 A | 4/1961 | Franck | |

(Continued)

FOREIGN PATENT DOCUMENTS

| | | |
|---|---|---|
| GB | 2213732 | 8/1989 |
| WO | 9930633 | 6/1999 |

OTHER PUBLICATIONS

Patent Cooperation Treaty, International Search Report issued for PCT/US2014/036737, dated Oct. 10, 2014, 3 pages Oct. 10, 2014.

*Primary Examiner* — Ellen C Hammond
*Assistant Examiner* — Christina Negrellirodrigue
(74) *Attorney, Agent, or Firm* — Bryan Cave LLP

(57) ABSTRACT

Syringe tips for use with dental syringes, connectors for connecting syringe tips to a dental syringe, and combinations thereof are described. In one embodiment, a syringe tip has an elastic inner tube with a flexible proximal portion extending proximally beyond a shoulder of an outer tube. An elongate fluid passageway extending from an entrance at the proximal end of the inner tube's flexible proximal portion to an exit at the distal end of the inner tube. The outer tube defines at least a portion of at least one additional elongate fluid passageway. In another embodiment, a syringe tip as described above is provided in combination with a connector that includes a tubular shaped portion adapted to be received within the fluid passageway of the inner tube and wherein the distal end of the tubular shaped member includes fingers adapted to radially expand the inner tube over the tubular shaped member.

22 Claims, 7 Drawing Sheets

(56) References Cited

U.S. PATENT DOCUMENTS

| | | |
|---|---|---|
| 3,140,106 A | 7/1964 | Thomas et al. |
| 3,184,706 A | 5/1965 | Atkins |
| 3,254,646 A | 6/1966 | Staunt et al. |
| 3,287,033 A | 11/1966 | Currie |
| 3,361,449 A | 1/1968 | Parro |
| 3,361,460 A | 1/1968 | Jansen |
| 3,394,954 A | 7/1968 | Sarns |
| 3,423,109 A | 1/1969 | New et al. |
| 3,454,290 A | 7/1969 | Tairraz |
| 3,479,058 A | 11/1969 | Chandler |
| 3,540,760 A | 11/1970 | Miller et al. |
| 3,563,575 A | 2/1971 | Sanford |
| 3,570,483 A | 3/1971 | Stram |
| 3,606,396 A | 9/1971 | Prosdocimo |
| 3,624,812 A | 11/1971 | Rosan, Sr. et al. |
| 3,653,689 A | 4/1972 | Sapy et al. |
| 3,659,880 A | 5/1972 | Goldsobel |
| 3,684,319 A | 8/1972 | Samartina |
| 3,698,088 A | 10/1972 | Austin, Jr. |
| 3,730,564 A | 5/1973 | Bachle et al. |
| 3,749,424 A | 7/1973 | Greene |
| 3,756,632 A | 9/1973 | Riggs et al. |
| 3,874,083 A | 4/1975 | Buckley |
| 3,958,818 A | 5/1976 | Mason |
| 3,973,752 A | 8/1976 | Boelkins |
| 3,980,325 A | 9/1976 | Robertson |
| 3,984,133 A | 10/1976 | Bird |
| 3,990,728 A | 11/1976 | Coughlin |
| 4,005,884 A | 2/1977 | Drori |
| 4,026,025 A | 5/1977 | Hunt |
| 4,032,177 A | 6/1977 | Anderson |
| 4,039,212 A | 8/1977 | Skarud |
| 4,063,760 A | 12/1977 | Moreiras |
| 4,076,279 A | 2/1978 | Klotz et al. |
| 4,109,943 A | 8/1978 | Cooke |
| 4,113,284 A | 9/1978 | Blocker |
| 4,133,564 A | 1/1979 | Sarson et al. |
| 4,138,145 A | 2/1979 | Lawrence |
| 4,149,315 A | 4/1979 | Page, Jr. et al. |
| 4,157,843 A | 6/1979 | Trnka |
| 4,178,023 A | 12/1979 | Guest |
| 4,187,848 A | 2/1980 | Taylor |
| 4,188,051 A | 2/1980 | Burge |
| 4,193,616 A | 3/1980 | Sarson et al. |
| 4,225,162 A | 9/1980 | Dola |
| 4,229,025 A | 10/1980 | Volgstadt et al. |
| 4,248,589 A | 2/1981 | Lewis |
| 4,249,899 A | 2/1981 | Davis |
| 4,257,629 A | 3/1981 | Maple et al. |
| 4,266,815 A | 5/1981 | Cross |
| 4,275,907 A | 6/1981 | Hunt |
| 4,278,279 A | 7/1981 | Zimmerman |
| 4,293,178 A | 10/1981 | Lee |
| 4,407,526 A | 10/1983 | Cicenas |
| 4,422,673 A | 12/1983 | Blackford et al. |
| 4,445,714 A | 5/1984 | Kisiel, III |
| 4,451,069 A | 5/1984 | Melone |
| 4,463,974 A | 8/1984 | Ergun |
| 4,481,697 A | 11/1984 | Bachle |
| 4,493,522 A | 1/1985 | Law |
| 4,522,435 A | 6/1985 | Miller et al. |
| 4,564,223 A | 1/1986 | Burrington |
| 4,565,392 A | 1/1986 | Vyse |
| 4,573,716 A | 3/1986 | Guest |
| 4,577,894 A | 3/1986 | Wake |
| 4,613,329 A | 9/1986 | Bodicky |
| 4,619,612 A | 10/1986 | Weber et al. |
| 4,621,842 A | 11/1986 | Kowal et al. |
| 4,637,639 A | 1/1987 | Jorgensen et al. |
| 4,676,749 A | 6/1987 | Mabille |
| 4,679,827 A | 7/1987 | Law |
| 4,705,304 A | 11/1987 | Matsuda et al. |
| 4,712,813 A | 12/1987 | Passerell et al. |
| 4,722,558 A | 2/1988 | Badoureaux |
| 4,750,765 A | 6/1988 | Cassidy et al. |
| 4,787,657 A | 11/1988 | Henniger |
| 4,793,637 A | 12/1988 | Laipply et al. |
| 4,807,911 A | 2/1989 | Short |
| 4,817,997 A | 4/1989 | Ingram |
| 4,826,431 A | 5/1989 | Fujimura et al. |
| 4,842,548 A | 6/1989 | Bolante |
| 4,893,846 A | 1/1990 | Mcgraw |
| 4,900,068 A | 2/1990 | Law |
| 4,903,995 A | 2/1990 | Blenkush et al. |
| 4,915,427 A | 4/1990 | Zahuranec |
| 4,923,228 A | 5/1990 | Laipply |
| 4,946,200 A | 8/1990 | Blenkush et al. |
| 4,951,976 A | 8/1990 | Boelkins |
| 4,958,858 A | 9/1990 | Guest |
| 4,969,668 A | 11/1990 | Sauer |
| 4,975,054 A | 12/1990 | Esrock |
| 4,984,984 A | 1/1991 | Esrock |
| 5,044,675 A | 9/1991 | Sauer |
| 5,048,872 A | 9/1991 | Gehring |
| 5,049,071 A | 9/1991 | Davis |
| 5,069,424 A | 12/1991 | Dennany, Jr. et al. |
| 5,125,835 A | 6/1992 | Young |
| 5,176,411 A | 1/1993 | DuPont, Jr. |
| 5,192,206 A | 3/1993 | Davis |
| 5,222,772 A | 6/1993 | Mcgraw |
| 5,236,356 A | 8/1993 | Davis |
| 5,242,300 A | 9/1993 | Esrock |
| 5,254,103 A | 10/1993 | Heuillon |
| 5,286,065 A | 2/1994 | Austin et al. |
| 5,306,146 A | 4/1994 | Davis |
| 5,320,389 A | 6/1994 | Dupont, Jr. |
| 5,342,195 A | 8/1994 | Davis |
| D352,354 S | 11/1994 | Davis |
| 5,370,423 A | 12/1994 | Guest |
| 5,433,485 A | 7/1995 | Austin, Jr. et al. |
| 5,460,619 A | 10/1995 | Esrock |
| 5,468,027 A | 11/1995 | Guest |
| 5,489,205 A * | 2/1996 | Davis ............... F16L 19/086 433/80 |
| 5,507,537 A | 4/1996 | Meisinger et al. |
| 5,591,389 A | 1/1997 | Esrock |
| 5,772,433 A | 6/1998 | Esrock |
| 5,927,975 A | 7/1999 | Esrock |
| 6,048,200 A * | 4/2000 | Martin ............... A61C 17/0202 433/80 |
| 6,113,391 A | 9/2000 | Esrock |
| 6,149,429 A | 11/2000 | Bukowski |
| 6,183,252 B1 | 2/2001 | Huang |
| 6,238,211 B1 | 5/2001 | Esrock |
| 6,250,921 B1 | 6/2001 | Esrock |
| 6,283,750 B1 | 9/2001 | Esrock |
| 6,319,001 B1 | 11/2001 | Esrock |
| 6,322,361 B1 | 11/2001 | Esrock |
| 6,533,578 B2 | 3/2003 | Segal |
| 2002/0039714 A1 | 4/2002 | Esrock |
| 2014/0329198 A1 | 11/2014 | Esrock |

* cited by examiner

FULL FLOW DISPOSABLE SYRINGE TIP AND CONNECTOR

RELATED APPLICATIONS

This application claims priority to U.S. Provisional Patent App. No. 61/819,114 filed May 3, 2013 and U.S. Provisional Patent App. No. 61/939,444 filed Feb. 13, 2014, the contents of which are incorporated herein by reference in their entirety.

FIELD OF THE DISCLOSURE

This invention relates to dental tools, and more particularly to a dental syringe and components thereof.

BACKGROUND

Dental syringes are hand-held devices for discharging fluids, such as pressurized air and water, into a patient's mouth. Such syringes are used by dentists and dental technicians for many dental procedures, including cleaning debris from a patient's teeth and mouth. The teeth and mouth are cleaned by spraying a stream of water, air or a combination of water and air from the syringe. A typical air-water syringe has a hand-piece, a syringe tip, and a connector adapted to releasably attach the syringe tip to the hand-piece.

Examples of connectors for use in connection with dental syringes include those described and disclosed in U.S. Pat. No. 5,927,975, U.S. Pat. No. 6,250,931, U.S. Pat. No. 6,283,750 and U.S. Pat. No. 6,319,001, which are incorporated herein by reference.

In operation, a syringe tip is received in a connector adapted to connect the tip to the hand-piece. Fluids are conveyed through the hand piece and the connector to the tip which delivers the fluids to the patient's mouth.

Historically, syringe tips were constructed entirely of metal. A typical metal syringe tip was a tube within a tube in which the inner tube served as a water passageway and the outer tube served as a passageway for air, both of which were in communication with air and water conduits of the hand-piece. Metal syringe tips are reusable, but require sterilization between uses.

Disposable syringe tips have begun to replace metal syringe tips as a more convenient option and one that may minimize the risk of spreading infectious diseases from one patient to another. As with metal syringe tips, a typical disposable air-water syringe tip has discrete air and water passageways for communication with air and water passageways of the hand-piece.

While disposable syringe tips offer some advantages over metal syringe tips, a typical disposable syringe tip may not perform as well as a typical metal syringe tip.

SUMMARY OF THE DISCLOSURE

Among the various aspects of the present disclosure are the provision of syringes tips for use with dental syringes, connectors for connecting syringe tips to the hand-piece of a dental syringe, and combinations thereof.

Briefly, in one aspect, the present disclosure is directed to a syringe tip that includes a flexible proximal portion configured to be slidably pushed onto a tubular shaped member with a fluid passageway therethrough, wherein the tubular shaped member is in fluid communication with a fluid passageway of the hand piece of a dental syringe. A pliable elongate tube (an inner tube) of resilient material extends substantially the entire length of the syringe tip. The flexible proximal portion is formed by that portion of the inner tube that extends proximally beyond a tube-support structure (outer tube) that surrounds the pliable tube and otherwise extends for most or all of the remaining length of the inner tube. An elongate fluid (e.g., water) passageway extends through the inner tube from the proximal end of the flexible proximal portion to its distal end. The elongate fluid passageway is adapted to communicate with the fluid passageway of the tubular shaped member when the flexible proximal portion of the syringe tip is on the tubular shaped member. The flexible proximal portion is sufficiently pliable to expand radially outwardly at its proximal end when it is pushed on the tubular shaped member, is sufficiently resilient to form a continuous seal around the tubular shaped member for sealing against fluid leakage between the tubular shaped member and the inner tube when fluid flows through the passageways within the syringe tip, and is sufficiently elastic to substantially recover its shape following deformation. In preferred embodiments, the outer tube has a stiffness greater than that of the inner tube and sufficient to maintain the inner tube in a selected operative position.

In another aspect, the present disclosure is directed to a connector for use in combination with a syringe tip, including a syringe tip of the disclosure.

Other objects and features of the present invention will be in part apparent and in part pointed out hereinafter.

DETAILED DESCRIPTION

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the disclosure pertains. Although a number of methods and materials similar or equivalent to those described herein can be used in the practice of the present disclosure, the preferred materials and methods are described herein.

All numbers expressing quantities or measurements of constituents and so forth used in the specification and claims are to be understood as being modified in all instances by the term "about." Notwithstanding that the numerical ranges and parameters setting forth the broad scope of the subject matter presented herein are approximations, the numerical values set forth in the specific examples are reported as precisely as possible. All numerical values, however, inherently contain certain errors necessarily resulting from the standard deviation found in their respective testing measurements.

Syringe tips for use with dental syringes, connectors for use with dental syringes, and combinations thereof are described. In the following description, for purposes of explanation, numerous specific details are set forth in order to provide a thorough understanding of various embodiments. It will be evident, however, to one of ordinary skill in the art that embodiments of the invention may be practiced without these specific details.

Figure 1:
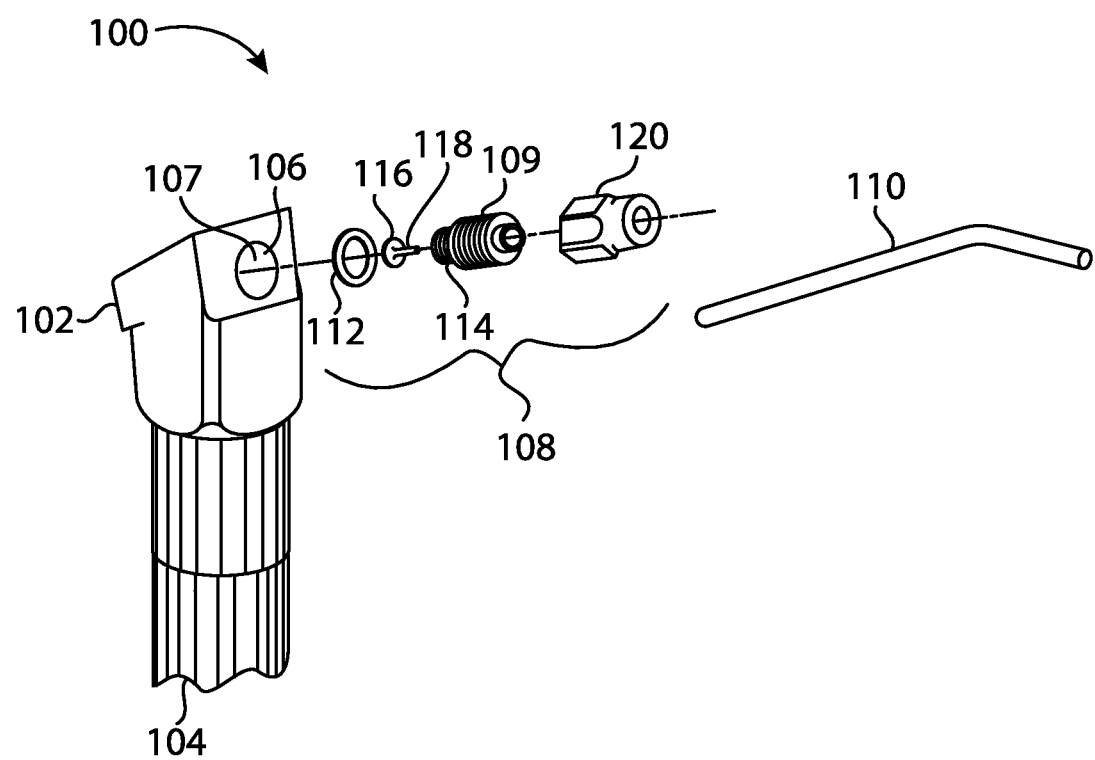
FIG. 1 is an illustration of an embodiment of a dental syringe.

FIG. 1 illustrates component parts of a dental syringe 100 for delivering fluids to a mouth of a patient. The syringe 100 includes a hand piece 102 shaped for gripping and having an intake end 104 and a discharge end 106. Discharge end 106 includes a threaded socket 107 adapted to receive a connector 108. Connector 108 is adapted for releasably connecting a syringe tip 110 to the hand piece 102. The syringe tip 110 has one or more interior passages for transporting fluids to the patient.

Connector 108 includes a body 109. O-ring 112, when the dental syringe is assembled, is circumferentially positioned around the connector near a threaded back portion 114 of the body 109 to prevent leakage between the hand piece 102 and the body 109. Connector 108 also includes a tubular connector component 116 comprising a tubular shaped member 118 adapted to direct the flow of a fluid (e.g., water) from the hand portion 102 of the syringe into an interior passage of the syringe tip 110. Part 120 is a locking nut that releasably secures the syringe tip 110 within the connector 108. The components of connector 108 are shown for purposes of illustrating an embodiment of a connector. In other embodiments, connector may not include a locking nut, body may include a tubular shaped member as an integral component, or connector may otherwise vary from the specific components and assemblage of components illustrated in FIG. 1.

Figure 2:
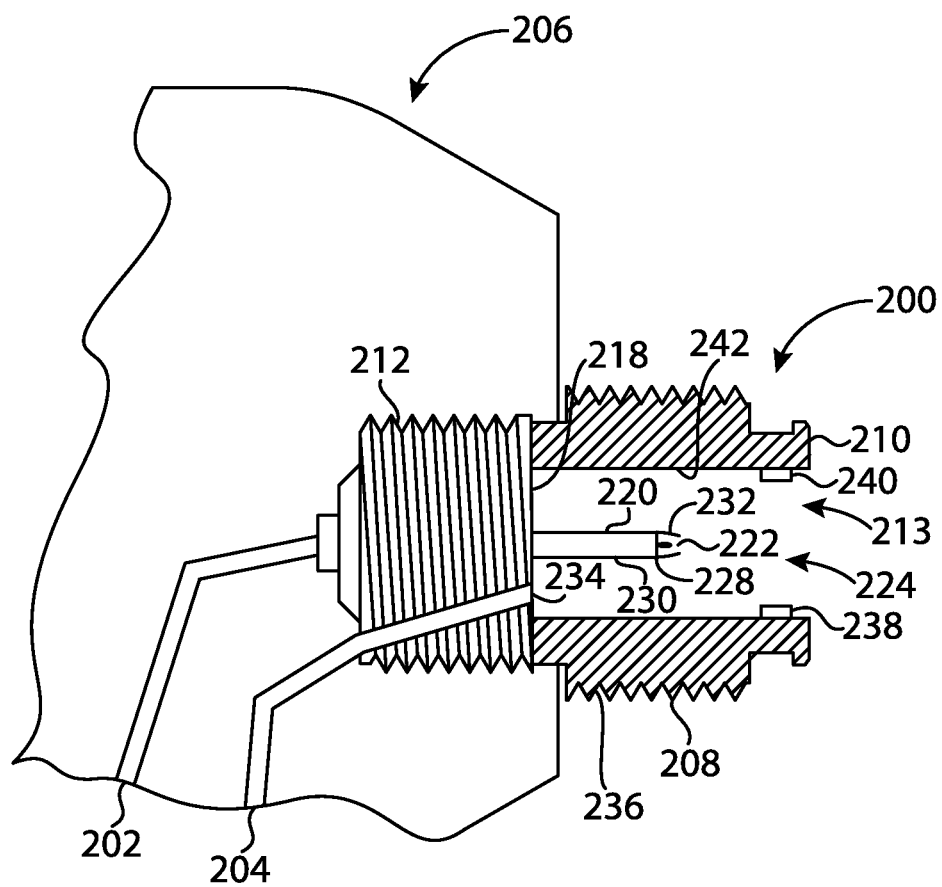
FIG. 2 is a side elevational view an illustration of an exemplary embodiment of a connector of the disclosure with portions broken away to show detail.

FIG. 2 illustrates an embodiment of a connector 200 of the invention adapted to alter or direct the flow of one or more fluids (e.g., water and air) from internal passageways 202, 204 of a hand piece 206 into corresponding fluid passageways of a dental syringe tip. Connector 200 has a generally cylindrical body 208 having a distal end 210 and an externally threaded proximal end 212 for attaching the fitting to the socket of hand piece 206.

Connector 200 includes a bottom 218 at the proximal end 212 of the body 208. Bottom 218 may be formed as part of the body or may be formed by a second piece, such as a generally cup-shaped collet coaxially received inside the proximal end 212 of the body 208, with the end wall of the collet forming the bottom of the body.

The body 208 has a central opening 213 sized and shaped for receiving a syringe tip. The opening 213 is generally cylindrical and has a larger diameter than the portion of the syringe tip to be received within the body. As discussed below, in some embodiments used in combination with a syringe tip of the disclosure, such portion of the syringe tip may be just the flexible proximal portion of the syringe tip or, in other embodiments, such portion may also include portions of the syringe tip distal to the flexible proximal portion. In an example embodiment, the opening has a diameter of about 0.157 inch to receive syringe tips with a diameter (as measured distal to the shoulder, if the syringe tip includes a shoulder) of about 0.153 inch. Other sizes of openings are used in other embodiments. For example, in another embodiment, the opening has a diameter of about 0.4 cm to receive syringe tips with a diameter (as measured distal to the shoulder, if the syringe tip includes a shoulder) of about 0.38 cm.

Connector 200 further includes a tubular shaped member 220, with an internal passageway 222, extending from the bottom 218 of the body 208 into a recess 224 of the body. A bore through the bottom 218 of the body is open to the first internal passageway 202 of the hand piece and to internal passageway 222. Therefore, in operation, a first fluid passes through internal passageway 202, through the bore, into the fluid passage 222, and out the tip 228 of the tubular shaped member 220. In the embodiment illustrated in FIG. 2, this first fluid is water.

The tubular shaped member 220 has a distal portion 230 sized for a sealing fit inside the central passageway of a syringe tip, such as a syringe tip of the present disclosure, described in detail below. The distal portion 230 further includes a plurality of fingers 232 extending distal to the tip 228 of the tubular shaped member and tapered inwardly toward the center of internal passageway 222.

Connector 200 also includes a stop 238, 240 within the recess 224 of the connector 200 adapted to engage a shoulder of a syringe tip of the disclosure when inserted into the recess 224. Stop 238, 240 is preferably located distally to the tubular shaped member 220 of the connector 200. More preferably, stop 238, 240 is located distally to the tip 228 of the tubular shaped member 220. Stop 238, 240 preferably narrows the size of the opening 213 to a diameter of less than the diameter of the syringe tip as measured distal to the shoulder but greater than the diameter of the flexible proximal portion of the syringe tip (such components of syringe tips of the disclosure being described in detail below). As illustrated in FIG. 2, stop 238, 240 may be formed as a protrusion, e.g., a continuous ridge or one or more raised portions. In other embodiments, a stop may be formed in, as, or affixed to an internal wall 242 of the connector 200.

In yet other embodiments, opening 213 is smaller than the outer diameter of the syringe tip, as measured distal to the shoulder; therefore, the distal end 210 of the connector is a stop that engages the shoulder of the syringe tip. In an example, the opening has a diameter of about 0.157 inch to receive syringe tips that include a shoulder with a diameter (as measured distal to the shoulder) of about 0.179 inch. In another example, the opening has a diameter of about 0.4 cm to receive syringe tips that include a shoulder with a diameter (as measured distal to the shoulder) of about 0.45 cm.

Connector 200 includes a second opening 234 in communication with a second internal passageway 204 of the hand piece. In operation, a second fluid passes through internal passageway 204, through opening 234, into the recess 224 of the body 208. In the embodiment illustrated in FIG. 2, this second fluid is air. Additional or alternatively-placed openings to receive air from internal passageway 204 into the recess 224 may be included in the bottom 218 of the connector 200.

Although opening 234 is on the bottom 218 of the connector in the embodiment illustrated in FIG. 2, in other embodiments, one or more openings to receive air from an internal passageway of a dental syringe hand piece may be disposed on the side of the connector, e.g., within a groove of a threaded proximal end of a connector.

A tubular shaped member of a connector of the invention is preferably circular. However, a tubular shaped member may be elliptical or formed in another shape suitable for enclosing a fluid passageway and receiving a fluid passageway of a syringe tip. A tubular shaped member may be substantially uniform in diameter (or applicable cross-sectional measure) throughout its length, such as tubular shaped member 220. Alternatively, a tubular shaped member may be wider at a lower (proximal) portion of the tubular shaped member, transitioning into a distal portion with a substantially uniform diameter, or it may taper along some portion or all of its length.

A tubular shaped member may be formed as a single piece with some portion or all of the bottom 218 of the body of the connector 200 (which, as noted above, may be formed as a single piece with the body of the connector or may be formed by a second piece) or the tubular shaped member may be formed as part of a tubular connector adapted to fit within, form a portion of, connect to, or rest upon the bottom of the connector.

Figure 3A:
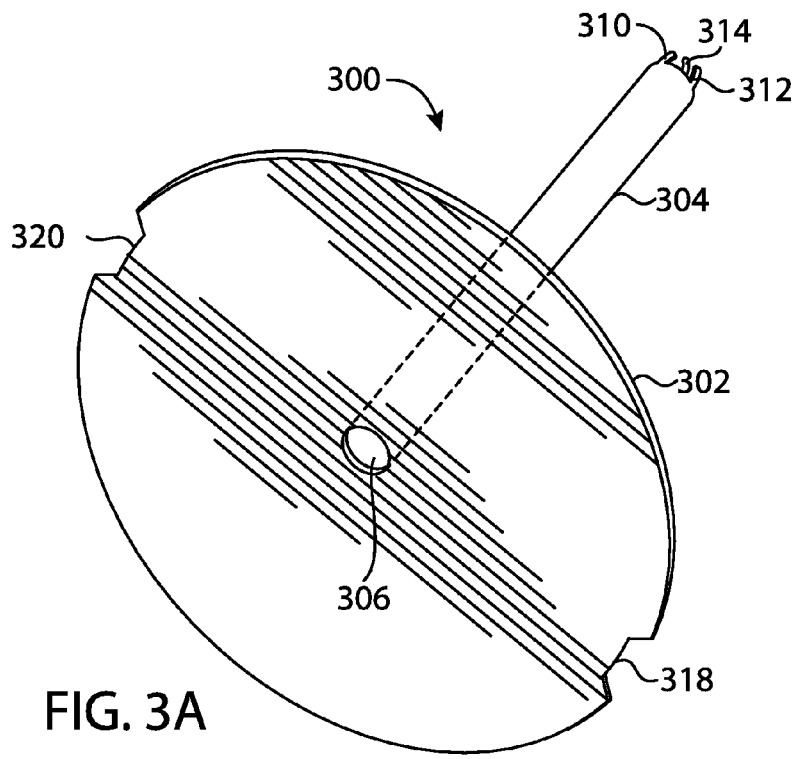
FIGS. 3A and 3B are end elevational views of an embodiment of a tubular connector component of a connector of the disclosure.
Figure 3B:
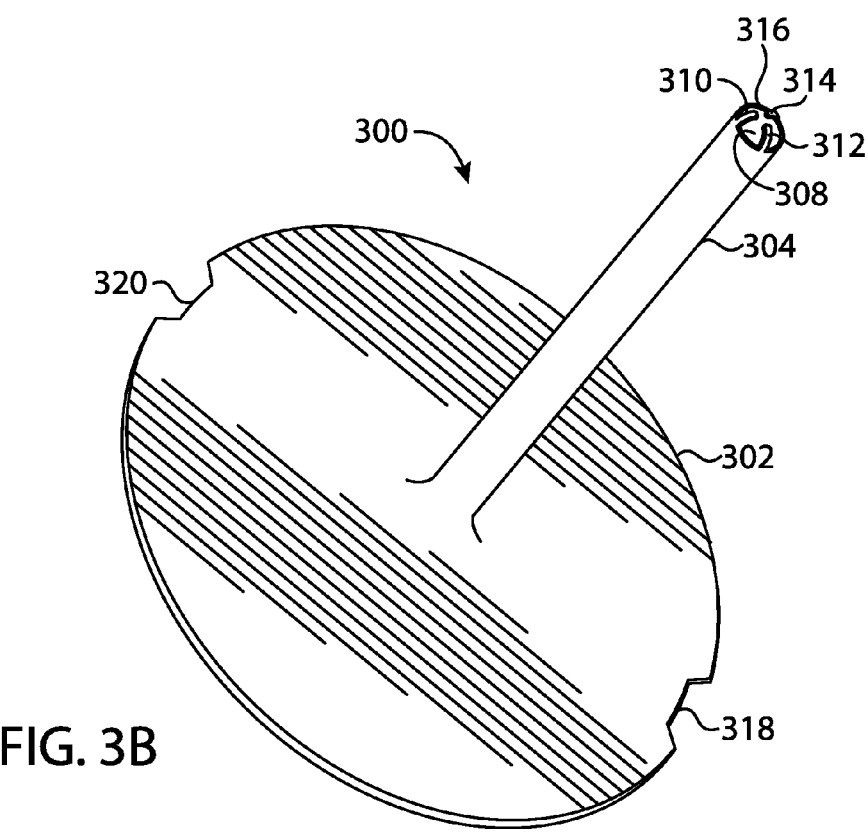

FIGS. 3A-3B illustrate an embodiment of a tubular connector component 300 which may be used in a connector, e.g., the connector 200 of FIG. 2. In this embodiment, the tubular connector 300 includes a substantially circular bottom portion 302 adapted to fit within the recess of the body of a connector and rest on the bottom of the body. Use of a collet to form the bottom of the connector is preferred for the embodiment of a tubular connector illustrated on FIG. 3 because the collet, and the tubular connector within the collet, can be removed through the bottom (proximal end) of the connector thereby facilitating removal and replacement of the tubular connector.

Tubular shaped member 304 extends distally from the bottom portion 302. Opening 306 in the bottom portion 302 is in communication with internal passageway 308 of the tubular shaped member 304.

Notches 318, 320 facilitate the flow of a second fluid (e.g., air) from the hand piece of a dental syringe into the recess of a connector.

Inwardly-tapered fingers 310, 312, 314 are disposed above the tip 316 of the tubular shaped member 304.

When disposed within an connector, opening 306 is open to a bore in the bottom of the connector, thus permitting fluid (e.g., water) to flow through an internal passageway of a hand piece, through the bottom of the connector, and into the internal passageway of the tubular shaped member.

As described in further detail below, when a syringe tip is seated onto a tubular shaped member 304, fingers 310, 312, 314 will stretch the interior fluid passageway of the syringe tip over the tip 316 of the tubular shaped member 304. Thus fingers 310, 312, 314 facilitate a tight, friction fit between the interior fluid passageway of the syringe tip and the tubular shaped member. Furthermore, fingers 310, 312, 314 facilitate accommodation of a tubular shaped member by an interior fluid passageway of a syringe tip having an internal diameter that is the same as or slightly smaller (when un-stretched) than the external diameter of the tubular shaped member, thereby facilitating an improved water flow through the dental syringe tip and into the mouth of a patient.

In the embodiment illustrated in FIGS. 3A and 3B, fingers 310, 312, 314 are formed as an integral a part of the tip 316 of the tubular shaped member 304.

Figure 6:
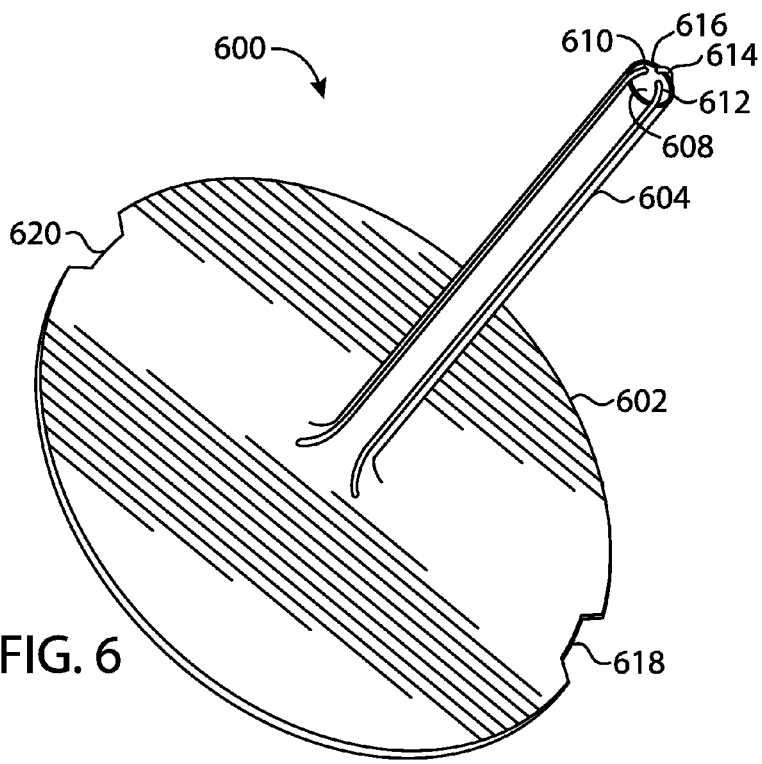
FIGS. 6 and 7 are end elevational views of alternative embodiments of tubular connector component of a connector of the disclosure.

In an alternative embodiment of a tubular connector 600, as illustrated in FIG. 6, fingers 610, 612, 614 are formed as ribs along the length of the outside of the tubular shaped member 604, terminating distally to the tip 616 of the tubular shaped member 604, and tapering inward toward the center of the internal passageway 608 of the tubular shaped member 604. As with the embodiment illustrated in FIG. 3, tubular connector includes a base 602 and notches 618, 620 adapted to be in fluid communication with a second fluid passageway of the hand piece of a dental syringe.

Figure 7:
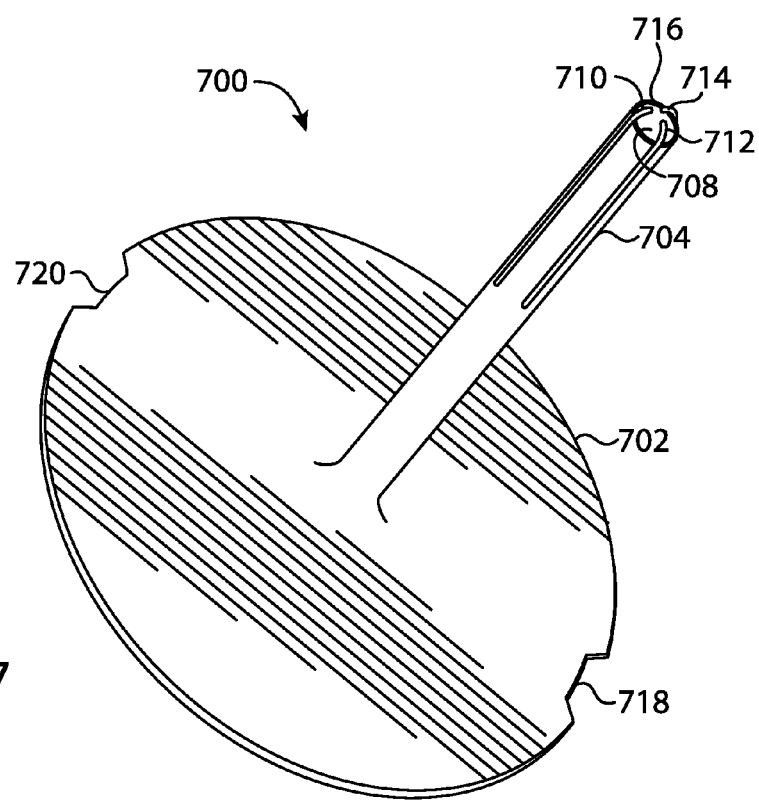

In the embodiment illustrated in FIG. 7, tubular connection 700 includes a base 702, notches 718, 720 adapted to be in fluid communication with a second fluid passageway of the hand piece of a dental syringe, and fingers 710, 712, 714 extending over the tip 716 of the tubular shaped member 704 of the tubular connector. In this embodiment, fingers 710, 712, 714 are affixed along a portion of the length of the outside of the tubular shaped member 704.

Although three fingers are illustrated in FIGS. 3A, 3B, 6, and 7 and are preferred, other embodiments include fewer or more than three fingers. For example, other embodiments include two, four, or five fingers. Yet another embodiment includes only one finger. An example embodiment includes one finger which is formed as an arc over the opening of the internal passageway of the tubular shaped member.

Fingers are preferably composed of one or more materials with sufficient strength to resist bending when a syringe tip is inserted over and onto the tubular shaped member of a connector. Such materials may include, for example, stainless steel or hard brass. In an embodiment in which a finger is formed as an integral part of the tip of a tubular shaped member, such finger is composed of the same material as the tubular shaped member (such as stainless steel or hard brass).

In certain preferred embodiments, fingers extend toward the center of the internal passageway of the tubular shaped member by an amount between 25 percent and 50 percent of the diameter of the internal passageway. In other embodiments, one or more finger extends toward the center of the internal passageway a distance of more than 50 percent of the diameter of the internal passageway. In yet other embodiments, one or more finger extends toward the center of the internal passageway a distance of less than 25 percent of the diameter of the internal passageway. Preferably, fingers do not materially impede the flow of water (or other fluid) through the internal passageway of the tubular shaped member of the connector or into an internal fluid passageway of a syringe tip. In certain preferred embodiments, fingers taper inwardly in a plane. In other embodiments, fingers taper inwardly in an arc. In some embodiments, the width of a finger is constant along its length; in other embodiments, the width of a finger tapers along its length, e.g., from the tip of the tubular shaped member to the tip of the finger. In certain embodiments, a finger, with a constant or tapered width, may have a rounded tip.

In example embodiments, a tubular shaped member with an external diameter of approximately 0.039 inches includes three tapered fingers, each of which extends in the range of approximately 0.03 to approximately 0.1 inches toward the center of the internal passageway of the tubular shaped member, and each of which is formed as an integral part of the top of the tubular shaped member.

In other example embodiments, a tubular shaped member with an external diameter of approximately 0.039 inches includes two tapered fingers, each of which extends in the range of approximately 0.03 to approximately 0.01 inches toward the center of the internal passageway of the tubular shaped member, and each of which extends along the exterior of the tubular shaped member and is affixed to the tubular shaped member, the bottom portion of the tubular connector, or both. In yet another example embodiment, a tubular shaped member with an external diameter of approximately 0.1 cm includes at least one finger which extends in the range of approximately 0.07 to approximately 0.025 cm toward the center of the internal passageway of the tubular shaped member, Other combinations of the various features of fingers described herein may be employed in other embodiments of connectors of the invention.

Tubular connectors 300, 600, 700 of FIGS. 3A and 3B, 6, and 7, respectively, are adapted to be held within the body of a connector at its proximal end. In another embodiment, a tubular connector includes a tubular shaped member adapted to be inserted through a bore (or other opening) in the bottom of an connector such that, in operation, a bottom portion of the tubular connector is disposed proximal to the bottom of the body of the connector. In yet another embodiment, a tubular connector includes an O-ring disposed at or near the proximal end of a tubular shaped member adapted to be received within a grooved opening in the bottom of a connector body; thus the tubular connector of such embodiment forms a portion of the bottom of the connector.

In an example embodiment, the tubular shaped member has a length in the range of approximately 0.085 to approximately 0.5 inches, e.g., approximately 0.085 inches, 0.1 inches, 0.15 inches, 0.2 inches, 0.25 inches, 0.3 inches, 0.35 inches, 0.4 inches, 0.45 inches, or 0.5 inches. In a particular embodiment, the tubular shaped member is approximately 0.085 inches long. In another embodiment, the tubular shaped member is approximately 0.125 inches long. In yet other example embodiments, the tubular shaped member is approximately 0.2 cm long, 0.4 cm long, 0.6 cm long, 0.8 cm long, 1.0 cm long, or 1.2 cm long. In some embodiments in which less than substantially all of the tubular shaped member is adapted to be disposed within a fluid passageway of a syringe tip, the dimensions described above may apply only to that portion of the tubular shaped member to be disposed within such fluid passageway; in other such embodiments, such dimensions apply to the entire length of the tubular shaped member.

In an example embodiment, the tubular shaped member has an external diameter in the range of approximately 0.032 inches to approximately 0.042 inches, e.g., approximately 0.032 inches, 0.035 inches, 0.038 inches, 0.040 inches, or 0.042 inches. In a particular embodiment, the external diameter of the tubular shaped member is approximately 0.039 inches. In another embodiment, the external diameter of the tubular shaped member is approximately 0.045 inches. In other example embodiments, the external diameter of the tubular shaped member is approximately 0.07 cm, 0.08 cm, 0.09 cm, 0.1 cm, or 0.11 cm. In some example embodiments in which the tubular shaped member tapers at its distal tip, the external diameter of such tapered tip portion may be smaller than the range described above within such tapered tip. Preferably, however, the tip does not taper to an external diameter of less than approximately 0.026 inches.

In embodiments in which the tubular shaped member includes a wider proximal portion and a narrower distal portion adapted to be disposed within a fluid passageway of a syringe tip, the above dimensions apply to such distal portion of the tubular shaped member.

In an example embodiment in which the tubular shaped member is tapered along all or a portion of its length adapted to be received in a fluid passageway of a syringe tip, the external diameter of the tubular shaped member varies along such length within the range of approximately 0.042 inches to approximately 0.026 inches.

A tubular shaped member may be further defined by the diameter of its internal passageway. In an example embodiment, the diameter of the internal passageway is in the range of approximately 0.026 inches to approximately 0.036 inches, e.g., approximately 0.026 inches, 0.028 inches, 0.030 inches, 0.032 inches, 0.034 inches, or 0.036 inches. In another example embodiment, the diameter of the internal passageway is approximately 0.06 cm, 0.07 cm, 0.08 cm, or 0.09 cm. In preferred embodiments, the diameter of the internal passageway is substantially constant along its length; in other embodiments, the diameter of the internal passageway may vary along its length, e.g., to accommodate a taper at the tip of the tubular shaped member.

In a preferred embodiment, a connector includes a tubular shaped member with an external diameter of approximately 0.039 inches along the distal portion of its length, wherein the tubular shaped member includes an internal passageway with a diameter of approximately 0.036 inches throughout the length of the internal passageway, and wherein the tubular shaped member further comprises a plurality of tapered fingers at the tip of the tubular shaped member.

Connectors of the invention may also include one or more features adapted to releasably secure a syringe tip within the recess of the connector, such as a locking nut, a gripping mechanism, compression O-ring, or other appropriate means, such as one or more of the features of syringe tip disclosed in U.S. Pat. No. 5,927,975, U.S. Pat. No. 6,250,931, U.S. Pat. No. 6,283,750 and U.S. Pat. No. 6,319,001.

Although the body 208 of the connector 200 illustrated in FIG. 2 is cylindrical, it may have other shapes such as hexagonal or elliptical. The body may be of one piece construction. Alternatively, the body may comprise multiple components. For example, a first component may include or house the fluid flow components of a connector. Such first component may include an externally threaded front end adapted to receive a second component, wherein the second component includes one or more additional features adapted to releasably secure a syringe tip.

As illustrated, connector 200 includes a distal threaded portion 236. Such portion may be adapted, for example, to receive a locking nut or second body part. In embodiments of a connector that do not include a nut or second body part, the threaded portion 236 may be omitted.

Although connectors of the invention may be used in connection with a variety of dental syringe tips, such connectors are particularly suited for use in connection with syringe tips of the present disclosure.

FIGS. 4A-4D illustrate an embodiment of a syringe tip 400 of the invention. Syringe tip 400 includes a proximal end 402 and a distal end 404. When used as a component of a dental syringe, as discussed in further detail below, the proximal end 402 of syringe tip 400 is inserted into a connector attached to the hand piece of a dental syringe.

Syringe tip 400 comprises a generally pliable elongate inner tube 406 of resilient material extending substantially the entire length of the tip and an outer tube 408, constituting an inner tube support structure.

Inner tube 406 of syringe tip 400 has a proximal end 410, a distal end 412, and an elongate fluid (e.g., water) tubular shaped central passageway 414 extending through the inner tube from its proximal end to its distal end.

The outer tube 408 surrounds the inner tube 406 and extends most of, but less than the entire, length of the inner tube 406. Accordingly, as illustrated in FIGS. 4A and 4C, the proximal end 410 of the inner tube 406 extends beyond the proximal end 414 of the outer tube 408 creating a flexible proximal portion 416.

Inner tube 406 has a fluted outer surface 417 with elongate flutes 418 spaced about the circumference of the outer surface, and elongate outer surface portions 420 each between adjacent flutes. The flutes 418 and outer surface portions 420 extend the length of the inner tube 406. The inner tube 406 fits snugly within the outer tube 408 and each elongate outer surface portion 420 is in substantially continuous contact with the inner surface 422 of the outer tube 408 generally along the entire length of the outer tube 408. Preferably, the inner and outer tubes 406, 408, respectively, are held together by a close friction fit between the outer surface portions 420 of the inner tube and the inner surface 422 of the outer tube. Alternatively, the tubes 406, 408 may be bonded together, e.g., by heat or with a suitable adhesive. The flutes 418 and the inner surface 422 of the outer tube 408 define elongate air passageways 424 circumferentially disposed about the elongate fluid passageway 414 (i.e., the central water passageway) and extending substantially the length of the outer tube.

Figure 4A:
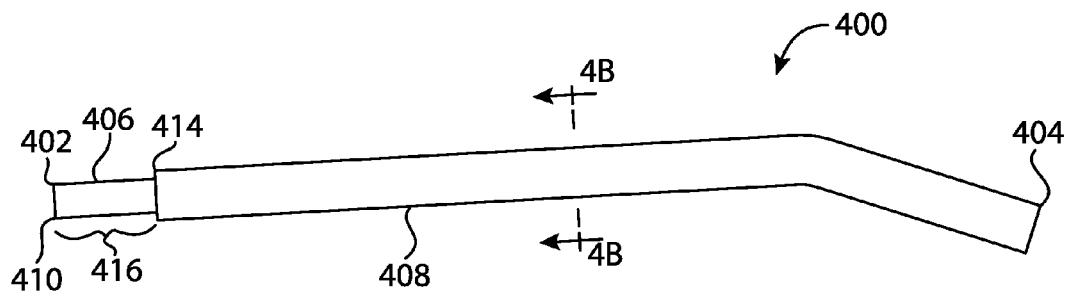
FIG. 4A is a side elevational view of an exemplary embodiment of a syringe tip of the disclosure.
Figure 4B:
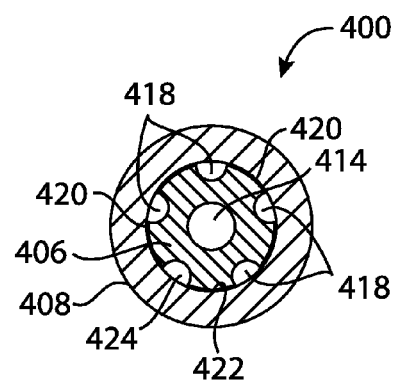
FIG. 4B is a vertical sectional view taken along the plane of line 4B-4B of FIG. 4A.
Figure 4C:
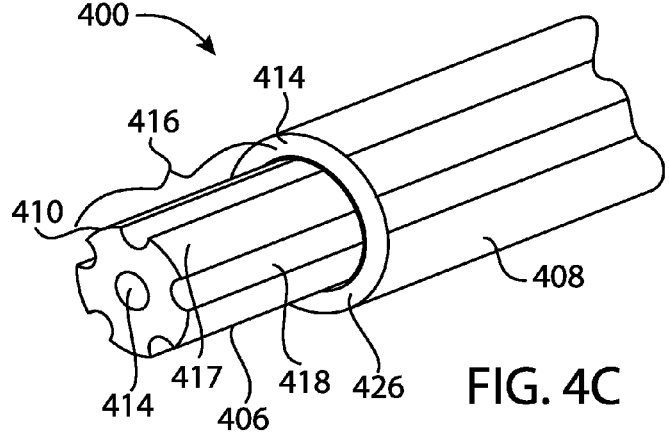
FIG. 4C is an end elevational view of the proximal end of the syringe tip of FIG. 4A.

Although the flutes in embodiment illustrated in FIGS. 4A-4C are in the outer surface of the inner tube, in an alternative embodiment, flutes are formed on the inner surface of the outer tube. In yet another embodiment, continuous passageways formed entirely within the outer tube serve as the elongate air passageways of a syringe tip. Five air passageways are illustrated in FIGS. 4B and 4C. Other embodiments include more than or fewer than five air passageways. For example, a particular embodiment includes six elongate air passageways. Although embodiments in which the disposition of the air passageways about the central passageway is substantially uniform are preferred, in other embodiments, placement of the air passageways is non-uniform.

Shoulder 426 is the proximal end 414 of, and formed as a part of, the outer tube 408. Shoulder 426 defines the distal end of the flexible proximal portion 416. Preferably, the shoulder is beveled, such that the intersection of the shoulder and the outer surface 417 of the inner tube 406 is chamfered. In other embodiments, however, the shoulder may be substantially flat.

The inner tube 406 of the syringe tip 400 is preferably made of a pliant medical grade polyvinyl chloride or other suitable synthetic resin having a durometer hardness reading between approximately 80 Shore A and 90 Shore A. Within this range, the inner tube is sufficiently pliable to seal against water leakage. The inner tube is also sufficiently elastic to substantially recover its shape following deformation. In preferred embodiments, the inner tube is capable of elastic deformation about the axis of the tip and perpendicular to the axis of the tip.

The flexible proximal portion of the tip, formed as a component of the inner tube, may be further defined by its elastic characteristics. In an example embodiment, following deformation perpendicular to the axis of the tip (e.g., by bending the flexible proximal portion to a position about 90 degrees from straight), the flexible proximal portion of the tip will recover to at least approximately 70% of its original state. In another example embodiment, the flexible proximal portion of the tip will recover to at least approximately 85% of its original state.

The outer tube 408 is preferably made of a stiffer medical grade polyvinyl chloride, having a durometer hardness reading of at least approximately 60 Shore D (most preferably 81 Shore D) and a flex modulus of at least approximately 10,000 psi (most preferably 12,000 psi). The outer tube 408 thus has a stiffness greater than that of the inner tube 406 and sufficient to maintain the entire syringe tip 400 in a selected operative position. Preferably, the outer tube 408 is sufficiently flexible to be capable of being bent by the operator to a selected operative position. The outer tube 408 is also sufficiently stiff (i.e., resistant to bending) such that the force of the fluid streams passing through a fluid passageway 424 during use do not substantially alter the shape the angle of the bend) of the tip. Because of this stiffness, a stream of air or water, or a mixed stream of both, can be directed to the specified desired location. For those embodiments in which the inner and outer tubes are both of polyvinyl chloride, there is an inherent adhesion between the tubes which resists movement of the inner tube relative to the outer tube. Although the tubes are preferably formed of polyvinyl chloride, in other embodiments, the tubes are formed of other suitable materials, such as resins.

As discussed in further detail below, the length of the flexible proximal portion 416 of a syringe tip may be defined by reference to components of the connector used in combination with the syringe tip. Generally, however, in certain preferred embodiments, flexible proximal portion of a syringe tip is at least approximately 0.25 inches long. In one embodiment, for example, the flexible proximal portion of the syringe tip is between approximately 0.25 inches and approximately 0.5 inches long (e.g., approximately 0.25 inches, 0.3 inches, 0.35 inches, 0.4 inches, 0.45 inches, or 0.5 inches long). In another example embodiment, the flexible proximal portion of the syringe tip is more than 0.5 inches long (e.g., approximately 0.6 inches, 0.7 inches, 0.8 inches, 0.9 inches, 1 inch, 1.1 inches, 1.2 inches, or 1.3 inches long). In yet another embodiment, the flexible proximal portion of the syringe tip is less than 0.25 inches long. In other example embodiments, the length of the flexible proximal portion is approximately 0.7 cm, 1.0 cm, 1.5 cm, 2.0 cm, 2.5 cm, or 3.0 cm.

The length of the flexible proximal portion may be further defined in reference to its elasticity. For example, in an embodiment, the length of the flexible proximal portion is sufficient to accommodate a rotational deformation (e.g., deformation about the axis of the tip) of at least approximately 45%.

In some embodiments, the length of the flexible proximal portion is defined relative to its inner diameter. For example, in some embodiments, the ratio of the inner diameter (ID) of the flexible proximal portion to its length (L) is less than approximately 0.15 (calculated as ID/L). In certain preferred embodiments, the ratio of the inner diameter of the flexible proximal portion to its length is less than approximately 0.15 and greater than approximately 0.025. In yet other embodiments, the ratio of the inner diameter of the flexible proximal portion to its length is less than approximately 0.08 and greater than approximately 0.03. In an example embodiment, the ratio of the inner diameter of the flexible proximal portion to its length is approximately 0.07.

Figure 4D:
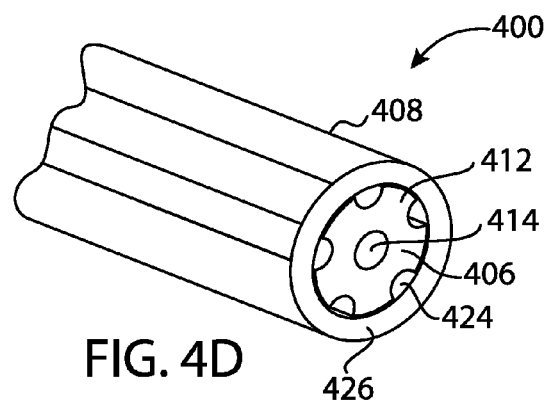
FIG. 4D is an end elevational view of the distal end of the syringe tip of FIG. 4A.

In the embodiment illustrated in FIG. 4D, the distal end 426 of the outer tube 408 is substantially co-terminus with the distal end 412 of the inner tube 406. In other embodiments, the distal end of the inner tube extends slightly beyond the distal end of the outer tube. For example, in an embodiment the distal end of the inner tube extends beyond the distal end of the outer tube by approximately $\frac{1}{16}^{th}$ of an inch (or, in another embodiment, approximately 0.15 cm). Such an embodiment may provide a more effective water spray. For example, air spray from the outer tube of such an embodiment of the syringe tip may improve the shape of the water stream from the inner tube as compared to an embodiment in which the distal ends of the inner and outer tubes are coterminous.

A syringe tip of the present invention (e.g., the syringe tip 400) is preferably made by a dual-extrusion method. In an example embodiment of such method, a first material is extruded through a first die to form an inner tube. This die is configured such that extrusion of the first material through the first die forms an elongate tube with elongate flutes. The flutes extend along substantially the entire length of the tube. The fluted tube is then passed longitudinally through a second die while a second material is extruded through the second die and around the inner tube. The second die is configured so that the outer tube (sleeve) so formed fits snugly over the inner tube. The extruded tubes are then cut to length.

In an example embodiment, after the extruded tubes are cut to length, a portion of the outer tube is stripped from the inner tube to form a desired length of flexible proximal portion of the inner tube and create a shoulder at the proximal tip of the outer tube. Although any suitable method may be used to strip a portion of the outer tube, in a preferred embodiment, a parallel jaw clamp is attached to a double rod end pneumatic cylinder with a 1 inch stroke. Then, in series, the jaw clamp opens, the jaws move forward and close on a length of extruded tube (which may be secured by a clamp or other appropriate means), the jaws rotate, retract, and then open thereby creating the flexible proximal portion of the syringe tip and a chamfered shoulder of the outer tube.

Figure 5A:
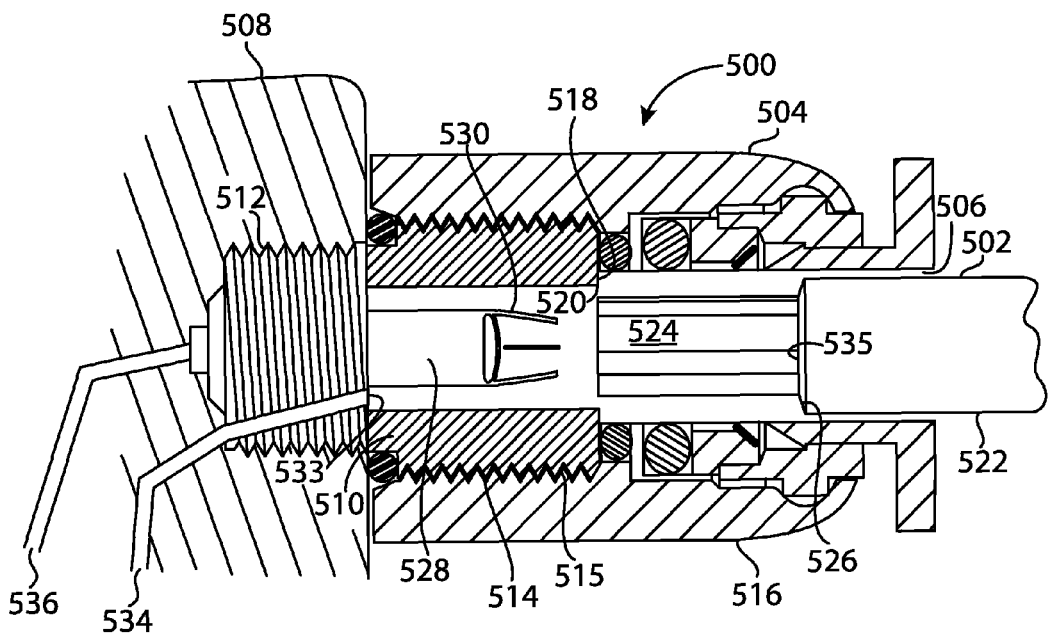
FIGS. 5A-5C are side elevations views of an exemplary embodiment of a syringe tip in combination with a connector of the disclosure with portions broken away to show detail.
Figure 5B:
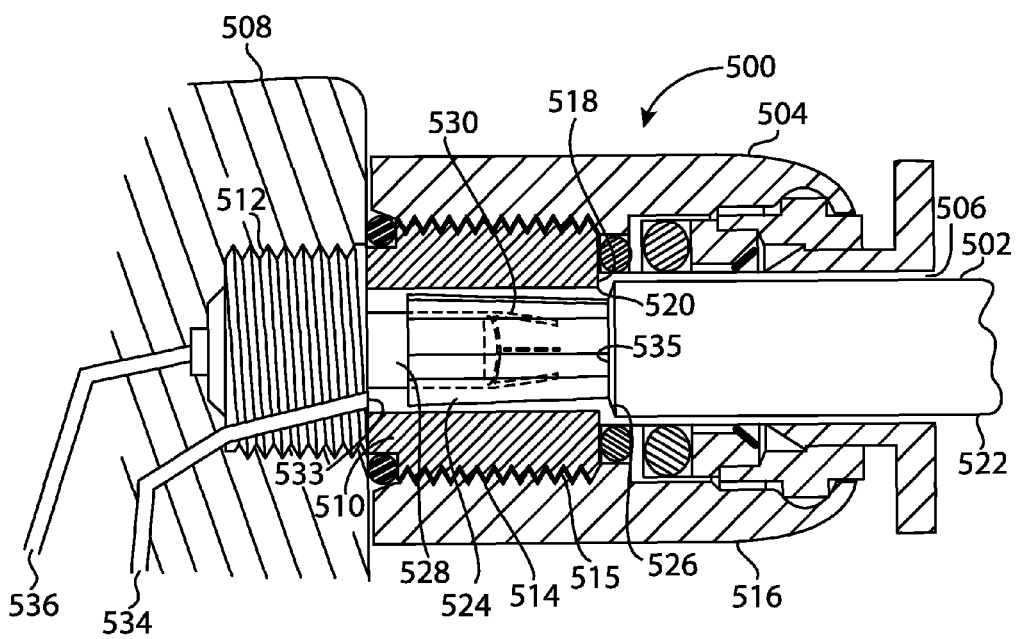
Figure 5C:
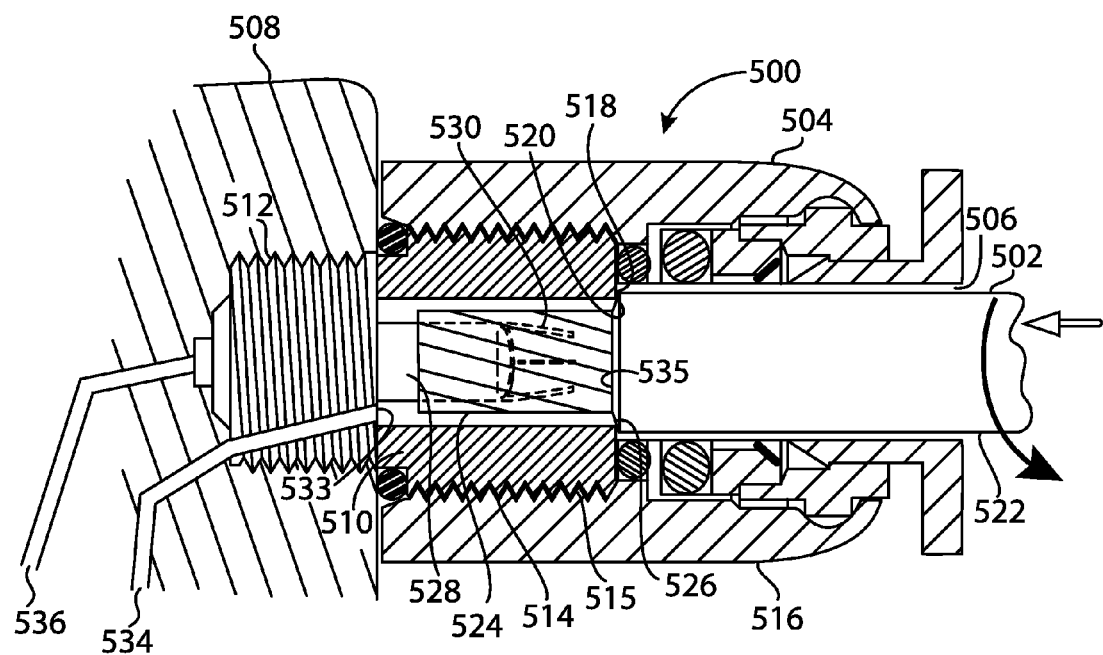

FIGS. 5A, 5B, and 5C illustrate, in combination 500, a syringe tip 502 and connector 504 of the invention. FIG. 5A illustrates a syringe tip being inserted into the recess 506 of connector 504 attached to a hand piece 508 of a dental syringe. In the embodiment of a connector 504 illustrated in FIGS. 5A-5C, the body of the connector 504 is composed of a first (proximal) body part 510 which includes a threaded exterior proximal portion 512 adapted to be received within the hand piece 508 and a threaded exterior distal portion 514 adapted to receive an internally threaded portion 515 of a second (distal) body part 516. In this embodiment, the stop 518 is formed by the distal edge 520 of the first body part 510, when used in combination with the second body part 516. The stop is preferably sized to avoid blocking air passageways within or formed in whole or in part by the outer tube of a syringe tip.

Specifically, in reference to the syringe tip 502 of combination 500, the distal portion of recess 506 (the portion of recess 506 formed by the second body part 516) is large enough to receive the outer tube 522 of syringe tip 502. The proximal portion of the recess 506 is large enough to receive the flexible proximal portion 524 of syringe tip 502 but stop 518 will engage the shoulder 526 of the syringe tip and function as an internal stop to prevent over-insertion of the syringe tip 502.

Second body part 516 may include one or features adapted to releasably secure the tip within the connector.

FIG. 5B illustrates combination 500 as the flexible proximal portion 524 of syringe tip 502 is pushed forward onto the tubular shaped member 528 of the connector. Fingers 530 radially stretch the interior fluid passageway of the flexible proximal portion 524.

Air enters the recess 506 though opening 533 in communication with internal air passageway 534 of hand piece 508 and enters one or more air passageways of the syringe tip 502 at the shoulder 526.

In general, stretching the interior fluid passageway of the inner tube may tend to flatten flutes formed in the outside wall of the inner tube. If the interior fluid passageway of the inner tube is stretched at a portion surrounded by the outer tube, such flattening of the flutes may thereby narrow air passageways formed in part by such flutes. However, because stop 518 is distal to the tip 532 of the tubular shaped member 528, and, therefore, shoulder 526 is distal to the tip 532 of the tubular shaped member 528 when the flexible proximal portion 524 of the syringe tip is seated on the tubular shaped member, there is little or no stretching of the interior fluid passageway of the inner tube at or beyond the stop. Accordingly, air flow to and within the air passageways is generally unimpeded by the stretched flexible proximal portion of the syringe tip.

FIG. 5C illustrates combination 500 when the syringe tip 502 is fully seated onto the tubular shaped member 528 of the connector. Preferably, syringe tip 502 is twisted as it is pushed onto tubular shaped member 528, thereby promoting a better connection between the interior fluid passageway of the syringe tip 502 and the tubular shaped member 528.

When combination 500 is in use with a hand piece of a dental syringe, the operator selects the fluid stream or combination of fluid streams (e.g., air, water, or an air-water mixture) to be delivered to the patient. The water stream, if selected, flows from the pressurized source through the water conduit 536 of the hand-piece 508 into the internal passageway of the tubular shaped member 528. The water then passes into the interior fluid passageway of the syringe tip 502 mounted on the tubular shaped member contained within the flexible proximal portion 524 of the syringe tip 502. The water is discharged from the distal end of the interior fluid passageway at the desired location. The resilient inner tube prevents or minimizes water leakage between the tubular shaped member 528 and the inner tube as long as part of the tubular shaped member is within the inner tube. Thus, the inner tube will prevent or minimize leakage even if the tip is not fully pushed onto the tubular shaped member and may be turned or rotated on the nipple with little or no leakage.

The air stream, if selected, flows from the pressurized source through the air conduit 534 of the hand-piece 508 into the recess 506 by way of opening 533. The pressurized air passes from the recess into the air passageways 535 at the shoulder 526 of the syringe tip 522, which are in fluid communication with the central bore. The air is discharged from the distal end of the syringe tip 502 to atomize the water discharged from the inner tube.

Syringe tips of the present disclosure, and, in combination, syringe tips and connectors of the present disclosure, offer significant advantages over traditional syringe tips and syringe tips in combination with connectors. The flexible proximal portion of a syringe tip freely twists and bends, even when the outer tube of the syringe tip is secured within a connector or when the syringe tip has been pushed onto a tubular shaped member of a connector. Therefore, the syringe tip may be twisted to tighten the seal between the tubular shaped member and the internal fluid passageway without altering (or with minimal alteration of) the placement of the distal end of the syringe tip relative to the hand piece of the dental syringe. The stronger seal between internal fluid passageway and tubular shaped member provided when a dental syringe of the disclosure is seated on the tubular shaped member using the push and rotate described above withstands increased water pressure flowing from the hand piece of the dental syringe (relative to traditional syringe tips) and prevents or minimizes leaking at the connection.

Introduction of air passageways at a shoulder distal to the proximal tip of the syringe tip (and, preferably, distal to the end of the tip of the tubular shaped member when disposed within the interior fluid passageway of the syringe tip) minimizes or eliminates air flow restriction within the air passageways in comparison to a traditional syringe tip in which a stiff outer tube is coterminous with an pliable inner tube. In addition, such separation of entry points for water and air passageways minimizes excess water moisture within the air spray.

Fingers at the distal end of a tubular shaped member in combination with a syringe tip comprising a flexible proximal portion of the inner tube facilitates use of a larger fluid (e.g., water) passageway through the tubular shaped member, thereby facilitating an improved water flow in comparison to traditional syringe tips.

When used in combination with certain traditional syringe tips, a damaged tubular shaped member (e.g., a tubular shaped member with a burr on its tip) may impair the function of the dental syringe. For example, a traditional syringe tip in which the fluid passageway is made of metal may not readily seat on a damaged tubular shaped member and, if forced, may only further damage the tubular shaped member. A traditional syringe tip with a pliable inner core, but lacking the flexible proximal portion, may seat onto a damaged tubular member, but the damaged tubular member may shred the soft inner core as the tip is rotated and pushed into place, thereby destroying the integrity of the seal and causing leakage. In contrast, a syringe tip of the present disclosure that includes a flexible proximal portion will twist or bend to accommodate the damaged tubular member, thereby eliminating or minimizing stripping and water cross over.

Similarly, and unlike traditional syringe tips, a syringe tip of the present disclosure that includes a flexible proximal portion will readily accommodate, and form a seal with, a tubular shaped member that is off-center within a connector.

The internal diameter of the proximal portion of a connector is largely dictated by the size of the threaded socket of a traditional hand piece; therefore, such diameter limits the diameter of a syringe tip that can be inserted therein. By including a flexible proximal portion, the diameter of syringe tip distal to the flexible proximal portion (and disposed outside of the portion of the connector in which diameter is dictated by the size of the hand piece socket) can be larger than the diameter of a traditional syringe tip. A syringe tip with a larger diameter where engaged by a retention mechanism within a connector will be more resistant to rotation than a traditional syringe tip.

Although the tubular devices are described herein as being syringe tips for dental syringes, it is to be understood that tubular devices of the present invention may have uses in various other aspects of the medical field.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A syringe tip for delivering a first and second fluid to a patient, the syringe tip comprising:
    a proximal end configured to be connected to a dental syringe and a distal end;
    an elastic inner tube extending substantially the entire length of the syringe tip, wherein the inner tube comprises a flexible proximal portion and a first elongate fluid passageway extending from a first fluid passageway entrance at a proximal end of the flexible proximal portion to a first fluid passageway exit at a distal end of the inner tube;
    an outer tube surrounding the inner tube and extending from a proximal end of the outer tube to a distal end of the outer tube, wherein the distal end of the outer tube is substantially coterminous with the distal end of the inner tube, wherein the outer tube comprises a shoulder at the proximal end of the outer tube and wherein the shoulder is at a distal end of the flexible proximal portion of the syringe tip; and
    a second elongate fluid passageway extending from a second fluid passageway entrance at the shoulder to a second fluid passageway exit at the distal end of the outer tube, wherein at least a portion of the second fluid passageway is defined by the outer tube.

2. The syringe tip of claim 1 wherein the length of the flexible proximal portion of the syringe tip is between is between approximately 0.25 inches and approximately 0.5 inches.

3. The syringe tip of claim 1 wherein the first fluid passageway entrance of the flexible proximal portion of the syringe tip is adapted to receive a tubular shaped member of a dental syringe connector and wherein the length of the flexible proximal portion of the syringe tip is greater than the length of the tubular shaped member received within the first fluid passageway.

4. The syringe tip of claim 3 wherein the flexible proximal portion is sufficiently pliable to expand radially outwardly when it is pushed onto the tubular shaped member and sufficiently resilient to form a continuous seal around the tubular shaped member.

5. The syringe tip of claim 1 wherein the second fluid passageway is defined by an outer surface of the inner tube and an inner surface of the outer tube.

6. The syringe tip of claim 5 further comprising a plurality of additional elongate fluid passageways extending from the shoulder to the distal end of the outer tube wherein such additional passageways are defined by the outer surface of the inner tube and the inner surface of the outer tube.

7. The syringe tip of claim 1 wherein the inner tube is sufficiently pliable to expand radially outward when the flexible proximal portion is pushed on a tubular shaped member of a dental syringe.

8. The syringe tip of claim 1 wherein the outer tube has a stiffness greater than the inner tube wherein the stiffness of the outer tube is sufficient to maintain the syringe tip in a selected operative position.

9. The syringe tip of claim 1 wherein the shoulder is beveled.

10. The syringe tip of claim 1 wherein the first fluid is water and the second fluid is air.

11. In combination, a syringe tip and a connector for releasably connecting the syringe tip to a hand piece for delivering a first and second fluid to a patient, the hand piece comprising a first fluid passageway for delivering a first fluid to a first fluid discharge end of the hand piece and a second fluid passageway for delivering a second fluid to a second fluid discharge end of the hand piece,
    the connector comprising:
        a tubular shaped member, the tubular shaped member comprising a fluid passageway extending from an opening in fluid communication with the first fluid discharge end of the hand piece to an exit at a distal end of the tubular shaped member and a plurality of fingers extending over the distal end of the tubular shaped member; and a second fluid opening in fluid communication with the second fluid discharge end of the hand piece;

the syringe tip comprising:
a proximal end configured to be connected to a dental syringe and a distal end;
an elastic inner tube extending substantially the entire length of the syringe tip, wherein the inner tube comprises a flexible proximal portion and a first elongate fluid passageway extending from a first fluid passageway entrance at a proximal end of the flexible proximal portion to a first fluid passageway exit at a distal end of the inner tube;
an outer tube surrounding the inner tube and extending from a proximal end of the outer tube to a distal end of the outer tube, wherein the distal end of the outer tube is substantially coterminous with the distal end of the inner tube, wherein the outer tube comprises a shoulder at the proximal end of the outer tube and wherein the shoulder is at a distal end of the flexible proximal portion of the syringe tip;
a second elongate fluid passageway extending from a second fluid passageway entrance at the shoulder to a second fluid passageway exit at the distal end of the outer tube, wherein at least a portion of the second fluid passageway is defined by the outer tube; and
wherein the flexible proximal portion is configured to be pushed onto the tubular shaped member and is sufficiently pliable to expand radially outward when pushed onto the tubular shaped member.

12. The combination of claim 11 wherein the connector further comprises a stop adapted to engage the shoulder of the syringe tip when the flexible proximal portion is pushed onto the tubular shaped member.

13. The combination of claim 12 wherein the connector comprises a bottom at a proximal end of the connector and wherein the distance from the bottom of the connector to the stop is equal to or greater than the length of the flexible proximal portion of the syringe tip.

14. The combination of claim 11 wherein the plurality of fingers taper over the fluid passageway exit at the distal end of the tubular shaped member a distance in the range of approximately 25 percent of the diameter of the exit to approximately 50 percent of the diameter of the exit.

15. The combination of claim 11 wherein the plurality of fingers arc over the fluid passageway exit at the distal end of the tubular shaped member a distance in the range of approximately 25 percent of the diameter of the exit to approximately 50 percent of the diameter of the exit.

16. The combination of claim 11 wherein the first fluid is water and the second fluid is air.

17. The syringe tip of claim 11 wherein the second fluid passageway is defined by an outer surface of the inner tube and an inner surface of the outer tube.

18. The syringe tip of claim 11 wherein the second fluid passageway is entirely within the outer tube.

19. The syringe tip of claim 17 further comprising a plurality of additional elongate fluid passageways extending from the shoulder to the distal end of the outer tube wherein such additional passageways are defined by the outer surface of the inner tube and the inner surface of the outer tube.

20. A method of assembling a dental syringe for delivering a first and second fluid to a patient, the method comprising:

providing a hand piece, the hand piece comprising a first fluid passageway for delivering a first fluid to a first fluid discharge end of the hand piece and a second fluid passageway for delivering a second fluid to a second fluid discharge end of the hand piece;

providing a connector, the connector comprising:
a tubular shaped member, the tubular shaped member comprising a fluid passageway extending from an opening in fluid communication with the first fluid discharge end of the hand piece to an exit at a distal end of the tubular shaped member and a plurality of fingers extending over the distal end of the tubular shaped member; and
a second fluid opening in fluid communication with the second fluid discharge end of the hand piece;

providing a syringe tip, the syringe tip comprising:
a proximal end configured to be connected to a dental syringe and a distal end;
an elastic inner tube extending substantially the entire length of the syringe tip, wherein the inner tube comprises a flexible proximal portion and a first elongate fluid passageway extending from a first fluid passageway entrance at a proximal end of the flexible proximal portion to a first fluid passageway exit at a distal end of the inner tube;
an outer tube surrounding the inner tube and extending from a proximal end of the outer tube to a distal end of the outer tube, wherein the distal end of the outer tube is substantially coterminous with the distal end of the inner tube, wherein the outer tube comprises a shoulder at the proximal end of the outer tube and wherein the shoulder is at a distal end of the flexible proximal portion of the syringe tip;
a second elongate fluid passageway extending from a second fluid passageway entrance at the shoulder to a second fluid passageway exit at the distal end of the outer tube, wherein at least a portion of the second fluid passageway is defined by the outer tube; and
wherein the flexible proximal portion is configured to be pushed onto the tubular shaped member and is sufficiently pliable to expand radially outward when pushed onto the tubular shaped member;

pushing the flexible proximal portion of the syringe tip onto the flexible proximal portion to form a seal between the flexible proximal portion and the tubular shaped member; and twisting the syringe tip to twist the flexible proximal portion, wherein the twisting and improves the seal between the flexible proximal portion and the tubular shaped member.

21. The method of claim 20 wherein the first fluid is water and the second fluid is air.

22. In combination, a syringe tip and a connector for releasably connecting the syringe tip to a hand piece for delivering a first and second fluid to a patient, the hand piece comprising a first fluid passageway for delivering a first fluid to a first fluid discharge end of the hand piece and a second fluid passageway for delivering a second fluid to a second fluid discharge end of the hand piece, the connector comprising:
a tubular shaped member, the tubular shaped member comprising a fluid passageway extending from an opening in fluid communication with the first fluid discharge end of the hand piece to an exit at a distal end of the tubular shaped member; and
a second fluid opening in fluid communication with the second fluid discharge end of the hand piece;

the syringe tip comprising:
- a proximal end configured to be connected to a dental syringe and a distal end;
- an elastic inner tube extending substantially the entire length of the syringe tip, wherein the inner tube comprises a flexible proximal portion and a first elongate fluid passageway extending from a first fluid passageway entrance at a proximal end of the flexible proximal portion to a first fluid passageway exit at a distal end of the inner tube;
- an outer tube surrounding the inner tube and extending from a proximal end of the outer tube to a distal end of the outer tube, wherein the distal end of the outer tube is substantially coterminous with the distal end of the inner tube, wherein the outer tube comprises a shoulder at the proximal end of the outer tube and wherein the shoulder is at a distal end of the flexible proximal portion of the syringe tip;
- a second elongate fluid passageway extending from a second fluid passageway entrance at the shoulder to a second fluid passageway exit at the distal end of the outer tube, wherein at least a portion of the second fluid passageway is defined by the outer tube; and
- wherein the flexible proximal portion is configured to be pushed onto the tubular shaped member and is sufficiently pliable to expand radially outward when pushed onto the tubular shaped member.

* * * * *